United States Patent
Herweijer et al.

(10) Patent No.: US 8,123,761 B2
(45) Date of Patent: Feb. 28, 2012

(54) DEVICE FOR REMOVING A TICK

(75) Inventors: Jan Philip Herweijer, Amsterdam (NL); Erika Balzarelli, Zürich (CH)

(73) Assignee: Meda AB, Pipers (SE)

( * ) Notice: Subject to any disclaimer, the term of this patent is extended or adjusted under 35 U.S.C. 154(b) by 823 days.

(21) Appl. No.: 11/665,292

(22) PCT Filed: Oct. 14, 2005

(86) PCT No.: PCT/NL2005/050015
§ 371 (c)(1),
(2), (4) Date: Aug. 27, 2008

(87) PCT Pub. No.: WO2006/041299
PCT Pub. Date: Apr. 20, 2006

(65) Prior Publication Data
US 2010/0191252 A1    Jul. 29, 2010

(30) Foreign Application Priority Data
Oct. 15, 2004    (NL) ..................................... 1027255

(51) Int. Cl.
*A61B 17/50*    (2006.01)
(52) U.S. Cl. ..................................... 606/131
(58) Field of Classification Search ............ 606/20, 606/22, 23, 25, 26, 131; 43/114, 133, 134, 43/900, 110, 111, 124, 125, 135, 136, 138; 294/99.2
See application file for complete search history.

(56) References Cited

U.S. PATENT DOCUMENTS

| | | | | |
|---|---|---|---|---|
| 3,809,294 A | * | 5/1974 | Torgeson | 222/182 |
| 4,976,718 A | * | 12/1990 | Daniell | 606/131 |
| 5,380,339 A | | 1/1995 | Webster | |

FOREIGN PATENT DOCUMENTS

| | | |
|---|---|---|
| DE | 20012032 U1 | 10/2000 |
| DE | 20307382 U1 | 7/2003 |
| WO | WO 95/00077 A | 1/1995 |

* cited by examiner

*Primary Examiner* — Ryan Severson
*Assistant Examiner* — Jonathan W Miles
(74) *Attorney, Agent, or Firm* — The Webb Law Firm, PC

(57) ABSTRACT

The invention relates to a device for removing a parasite from the skin of a host, wherein the device comprises engaging means for engaging the parasite and removing the parasite from the skin of the host, and wherein the device comprises fixation means for fixing the device on the skin of the host, wherein the engaging means are adapted for movement. The device is preferably provided with administering means for the purpose of supplying a cooling medium to at least the parasite. The invention also relates to a method for removing a parasite from the skin, comprising of engaging the parasite, removing the parasite from the skin of the host, supplying a cooling medium to the parasite, fixing the device on the skin of the host and moving the engaging means for the purpose of engaging the parasite.

17 Claims, 4 Drawing Sheets

DEVICE FOR REMOVING A TICK

BACKGROUND OF THE INVENTION

1) Field of the Invention

The present invention relates to a device for removing a parasite such as a tick from the skin of a human or animal functioning as host, wherein the device comprises engaging means for engaging the parasite and removing the parasite from the skin of the host.

2) Description of the Prior Art

A device for engaging ticks is otherwise known from DE-U-203 07 382, wherein a cooling aerosol is indeed applied, but wherein no fixation means are present.

It is noted here that in DE-U-200 12 032 a cap is present which is placed on the skin. The document states that the function of the cap is to protect the skin during administering of the cooling liquid. There is accordingly a small aperture present in the cap so that there is the smallest possible chance of the parasite being touched and performing an infective action when the device with the cap is placed over the parasite. The device according to this document can also be used without cap.

SUMMARY OF THE INVENTION

Such devices are known as tick pliers and tick tweezers. These have the drawback that, when the parasite is engaged by the engaging means, the parasite becomes irritated and will discharge at least a part of the content of its digestive organs into the bloodstream of its host. Because parasites are often infected with pathogens, such as the pathogens of Lyme's Disease, this is highly undesirable.

In order to avoid this, the present invention provides such a device which is provided with fixation means for fixing the device on the skin of the host parallel to the skin of the host at least during engaging of the engaging means, wherein the engaging means are adapted to move relative to the fixation means during engaging of the parasite.

As a result of these measures the device is positioned and fixed on the skin before the parasite is engaged, and only then is the parasite engaged. Because the device is already fixed when it engages, the chance of contacting the parasite prior to engagement, and thereby the danger of infection, is greatly limited; the parasite is after all only touched when it is engaged, whereafter it is immediately removed from the skin of the host. A better control of the engaging process is thus obtained. The process can moreover be performed more precisely.

The danger of infection still persists however, because a (short) period of time elapses between contacting the parasite and removal thereof from the skin. In order to further lessen this danger, a preferred embodiment of the invention is provided with administering means for the purpose of supplying a cooling medium to at least the parasite.

With this preferred embodiment of the invention it is possible to cool or freeze the parasite before it is engaged by the engaging means. In cooled or frozen state the parasite will hardly be able to perform any infective action, thus greatly reducing the danger of infection. Furthermore, the parasite is less likely to disintegrate, so that removal of the whole parasite is easier, and the danger of residues of the parasite being left behind in the skin of the host is greatly decreased.

The use of fixation means prevents displacement of the engaging means, and thereby contacting of the parasite, prior to cooling of the parasite.

Although the device according to the invention is suitable for application with parasites of many kinds which attach themselves to the skin of their host, the advantages of the invention are found to be particularly manifest in the case of ticks.

Parasites such as ticks which attach themselves to the skin of their host have a wide body which is connected with a narrow part to the body of their host. In order to remove the parasite from the body of its host, it is recommended to engage the parasite at the narrow part because, during movement away from the skin of the host, a leverage is obtained against the broad part of the parasite. So as to prevent the wide part of the parasite obstructing the engaging means when the engaging means are being positioned, it is recommended that the engaging means are adapted to move substantially parallel to the skin during engaging of the parasite.

Another preferred embodiment provides the measure that the engaging means comprise a substantially flat structure provided on its edge with a notch, wherein the notch is provided with two edges converging from the edge of the structure to a point and the engaging means comprise drive means for moving the structure relative to the fixation means in a direction enclosed between the edges of the notch. This measure leads to simplification of the construction of the device; prior art engaging members after all usually comprise two elements which approach the tick from either side. Owing to the construction according to this embodiment only a single engaging element is required. A fixation element is however necessary here to provide a fixed reference relative to the skin and relative to which the engaging element moves. The invention is not otherwise limited to this embodiment of the engaging elements; other engaging elements such as plier and tweezer-like forms can likewise be applied.

Because the engaging means have a limited thickness, they must be given a thin form. This brings with it the danger that when they engage the parasite they cut through the parasite, whereby the parts of the parasite remaining in the skin of the host can hardly be removed. In order to avoid this drawback, the edges of the flat structure which are located on the side of the notch are rounded.

The structure functioning as engaging means must carry out a defined movement relative to the fixation means. To this end the invention preferably provides the measure that the flat structure is connected to the fixation means for guidable movement by means of guide means. Guiding is here understood to mean defining the position of the strip relative to the fixation means during movement. This guiding function can be performed by slide guiding, but also by for instance a lever or a parallelogram mechanism.

A further preferred embodiment provides the measure that the fixation means comprise an element which is provided with an opening and which is adapted to be placed with a substantially flat side against the skin of the host, and that the guide means comprise a first part adapted to guide the flat structure slidably parallel to the flat side of the element at least at the position of the opening in the element. It hereby becomes possible to manufacture the construction from plastic. Modern design techniques for plastic make it possible to make the relevant components at low cost.

It is possible to give the guide means a converging form at one end. The converging path of the guide means is placed such that at the end of the movement of the strip functioning as engaging means the pieces situated on either side of the notch of the strip are moved toward each other, so that an additional enclosing movement is obtained. The engaging process is hereby improved. It is however necessary here that the strip be given a flexible form such that the pieces of strip can be moved toward each other.

Ticks and other parasites can strike unexpectedly in nature. It is therefore sensible to take a device according to the invention on walks in the countryside. In order to facilitate carrying thereof, it is attractive to give the device the most compact possible form. A preferred embodiment provides for this purpose the measure that the structure comprises a strip which is manufactured from flexible material and which is connected slidably to the guide means, that the guide means comprise a second part extending at a distance from the vicinity of the opening at an angle to the flat side, and that the first part of the guide means and the second part of the guide means are connected by a bent third part. These measures make it possible for the strip to bend and that the device can hereby extend in a direction at an angle to the surface which comes into contact with the skin. It hereby becomes possible to combine a device, which extends substantially transversely of the skin, with a small volume, so that the device according to the invention can be readily carried.

In order to facilitate operation of the strip, this latter preferably extends outside the element, and the strip is coupled outside the element to a drive member.

The administering means are preferably adapted to supply the cooling medium to the parasite in the form of an aerosol jet. The cooling effect is obtained due to the evaporation, i.e. the phase transition of the liquid. Dispensing is facilitated by supply of the liquid in the form of small droplets (an aerosol).

Yet another embodiment provides the measure that the administering means comprise an aerosol container, a valve placed thereon and a spray nozzle, wherein the spray nozzle is placed for directing the aerosol jet, which exits the nozzle when the valve is opened, inside the opening in the fixation means. These measures result in a simple construction.

In order to avoid excessive administering of the cooling aerosol, it is recommended that the aerosol can be administered in metered manner. It is recommended for this purpose that the valve placed on the aerosol container is a metering valve. Between the cooling medium leaving the container and reaching the parasite, the aerosol particles must travel a certain path. Because these liquid particles are subjected to a pressure decrease when they leave the aerosol container, they tend to evaporate. In order to prevent premature evaporation and to make the cooling effect as effective as possible, the spray nozzle is preferably adapted to generate an aerosol jet with large drops.

So as to optimize handling of the device, the aerosol container is substantially cylindrical and the cylinder axis of the aerosol container extends substantially parallel to the direction of movement of the strip outside the element. A structurally simple solution can be achieved in that the drive member is adapted to be guided by the aerosol container.

For use of the device according to the invention two operations have to be performed after placing of the device on the skin, i.e. administering of the cooling aerosol and removal of the parasite. To enable the first operation to be performed, an actuating element is preferably connected to the valve of the aerosol for the purpose of operating the valve with an axial movement of the actuating element.

In order to keep the construction of the device as simple as possible a housing is arranged around the aerosol container, the drive member is adapted to be guided between the aerosol container and the actuating element extends through the housing.

Most aerosol valves are adapted for opening by an axial movement. So as not to have to apply any specific, special constructions, which generally have the effect of increasing cost-price, the valve can be operated by an actuating element which can be operated from outside the housing and which is connected to a lever connected to the housing for rotation about an axis placed a distance from the valve.

The element is preferably substantially cylindrical, the axis of the cylinder corresponds to the axis of the aerosol housing, and the element is provided in its outer surface with an opening. A view of the parasite hereby becomes possible during use of the device, so that the user can observe what is happening to the parasite.

In order to have the best possible view of the tick during the removal operation, it is important that the opening through which the tick is observed is as large as possible. It is recommended for this purpose that the opening extends as far as the guide means. This entails that it is in fact only the guide means that form the connection between the aerosol housing and the fixation means.

It is also possible to manufacture at least a part of the housing from a transparent plastic, also in combination with an opening. The use of transparent plastic provides the option of forming the plastic such that a magnifying effect is obtained; the process taking place inside the element can hereby be more readily observed by the user.

According to another preferred embodiment, the device has a substantially cylindrical form, of which the end surface adapted to come into contact with the skin of the host extends at an angle other than 90° from the axis of the cylinder. This design results in a unit which is easy to handle, while the inclining surface results in an inclining position of the device. This inclining position makes it possible to observe the parasite through the opening in the cylindrical element, while a less tiring position of hand holding the device is achieved.

Yet another preferred embodiment provides the measure that the device is combined with a storage space for removed parasites. It hereby becomes possible to keep the removed parasites, so that it is possible to check whether the parasite is carrying pathogens and whether there is any danger of infection. This storage space can be formed by a space arranged in the body of the device, although the storage space can also be formed by a separate box which can be provided with different compartments.

The invention also relates to a method for removing a parasite such as a tick from the skin of a human or animal functioning as host, wherein the method comprises of engaging the parasite and removing the parasite from the skin of the host, and supplying a cooling medium to the parasite, wherein the method is characterized by fixing the device on the skin of the host in the direction parallel to the skin of the host at least during administering of the cooling medium, and moving the engaging means relative to the fixation means for the purpose of engaging the parasite. The same advantages are achieved with this method as with the measures according to the invention.

In order to prevent the parasite causing an infection before it is frozen or cooled, it is recommended that a cooling medium is supplied to the parasite before the parasite is engaged.

BRIEF DESCRIPTION OF THE DRAWINGS

The present invention will be elucidated hereinbelow with reference to the accompanying drawings, in which.

DETAILED DESCRIPTION OF THE PREFERRED EMBODIMENTS

Figure 1:
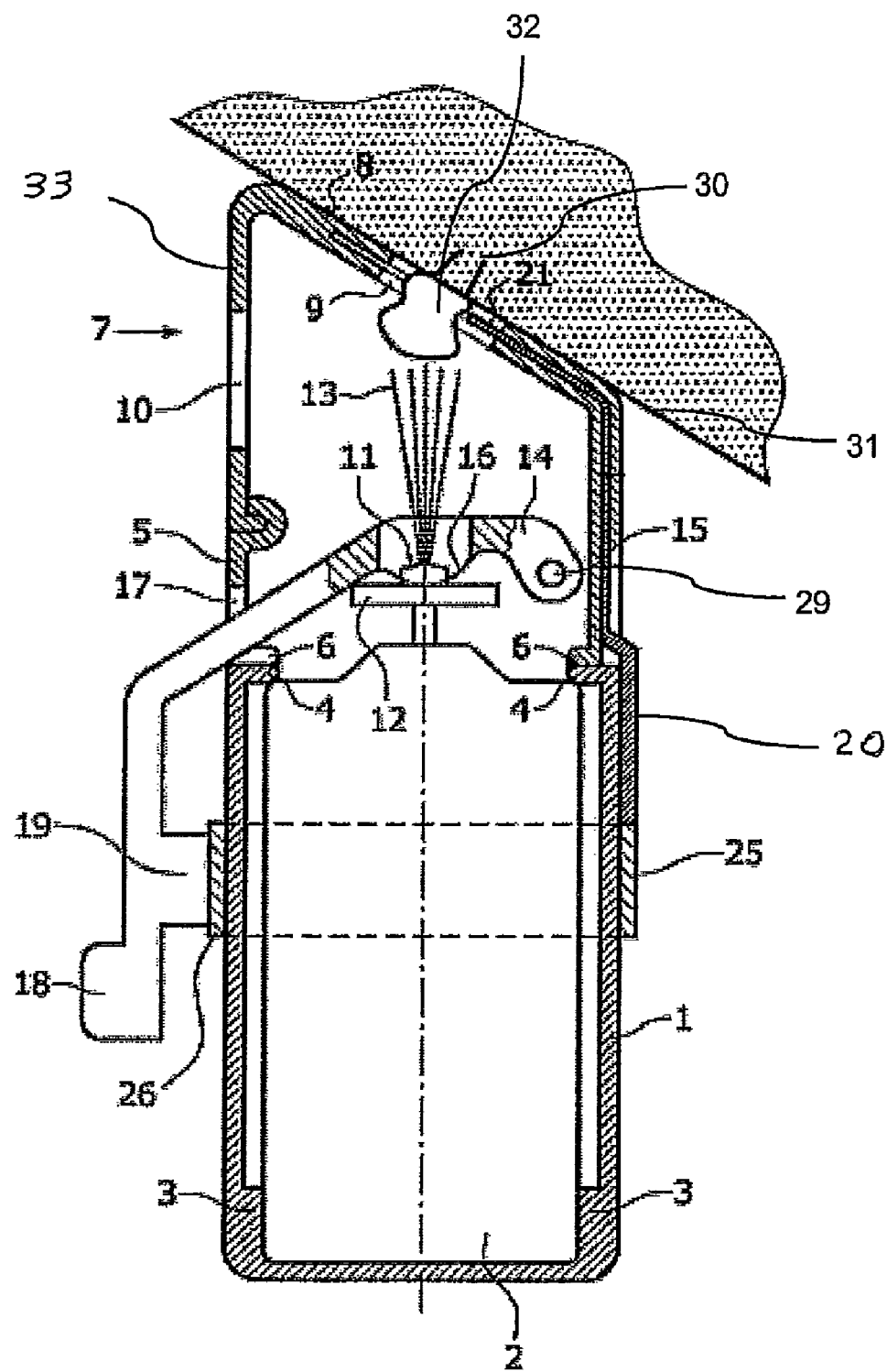
FIG. 1 shows a sectional view in lengthwise direction of a first embodiment of the invention.

The device according to the present invention comprises a substantially cylindrical housing 1 in which a likewise cylindrical aerosol container 2 is received. Positioning edges 3 and 4 are arranged in housing 1 to position aerosol container 2 in the housing, wherein the upper positioning edge 4 also fixes aerosol container 2 in housing 1. Housing 1 is preferably manufactured from plastic.

Arranged connecting onto housing 1 by means of a snap connection 6 is a coupling piece 5 which forms a continuation of the cylinder defining the housing 1. Coupling piece 5 is likewise preferably manufactured from plastic.

A fixation element 7 is arranged connecting onto coupling piece 5. The fixation element also extends within the cylinder defining the housing 1. The fixation element is closed on its distal end by an oblique fixation wall 8. Fixation element 7 is connected to coupling piece 5 by means of a snap connection. Fixation element 7 is preferably manufactured from transparent plastic.

An opening 9 is arranged in fixation wall 8, and an opening 10 is arranged in the cylinder surface wall of fixation element 7 on the side where the axial length of the cylinder surface wall is greatest.

Aerosol container 2 is provided with a valve 11 which is formed integrally with a spray nozzle. Valve 11 is opened by being pressed in axial direction. As is usual, valve 11 is constructed so that valve 11 is urged to the closed position by the pressure prevailing inside the aerosol container. For operation of the valve, the valve is provided with a collar 12. The nozzle of the valve is adapted to generate an aerosol jet 13 directed at opening 10.

A lever 14 is arranged for the purpose of operating the valve. Lever 14 is connected rotatably to coupling piece 5 by means of protrusions 15 which are arranged on coupling piece 5 and provided with projections which engage in recesses arranged in lever 14. Other pivoting constructions are also possible. Lever 14 is provided with an opening through which valve 11 extends. Lever 14 is further provided with a pair of protrusions 16 which are adapted to press in collar 12 when the lever is operated and to thereby open valve 11. Lever 14 extends further through an opening 17 arranged in coupling piece 5. The distal end of the lever extends substantially parallel to the axis of cylindrical housing 1. The lever is provided on the end with an actuating element 18. The lever is provided on its inner side with a blocking protrusion 19. The blocking protrusion 19 is not connected to actuator element 26, but instead serves to prevent the lever 14 from moving outside a working range of motion that could damage the apparatus.

Figure 2:
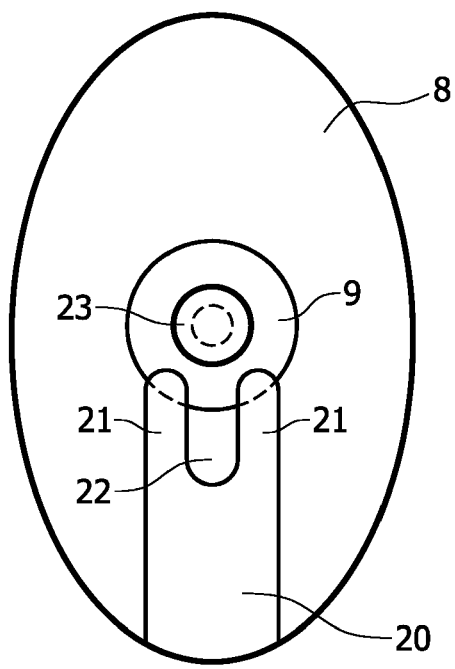
FIG. 2 shows a sectional view of the device according to the invention parallel to the skin of the host before the parasite is engaged.
Figure 3:
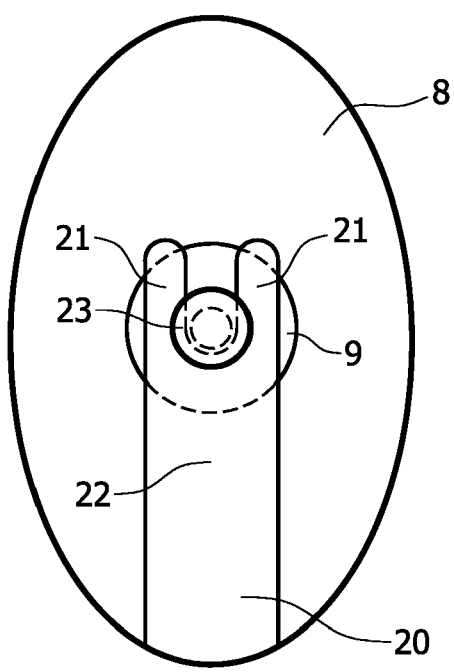
FIG. 3 shows a view corresponding to FIG. 2 after a parasite has been engaged.

As shown in FIGS. 2 and 3, the device according to the invention is adapted to engage a parasite with an engaging element which is adapted to be moved relative to fixation element 7. In the present embodiment the engaging element is formed by a strip 20 of flexible material, for instance plastic, which is arranged movably relative to the fixation element. Fixation element 20 is provided on its end with two tongue-like elements 21, between which a notch 22 is formed. Notch 22 converges from the edge of the end of fixation element 8 to a point. It is hereby easy to engage a parasite such as a tick 23. The tick is formed by a body 32 which attaches itself with its mouth 30 to the skin 31 of its host. The body 32 has a greater size than the mouth 30. This provides the possibility of placing the two tongues 21 on either side of the mouth 30 of the parasite, wherein the mouth extends in notch 22. This situation is shown in FIG. 3. The greater size of the body 32 makes it possible to remove the parasite by a movement with a component transversely of the direction of the skin 31.

In order to effect a good engagement between the skin of the host and the body of the parasite the strip on the side of the notch must be thin. A consideration to be taken into account is that the edge may not be sharp so as to prevent the parasite being severed; the solution thus lies in a thin strip with rounded edge on the side of the notch.

The starting point for reaching the situation shown in FIG. 3 is the situation shown in FIG. 2. For this purpose the strip forming engaging element 21 must be moved in its longitudinal direction. The device according to the invention makes this movement possible by applying a strip 20 of flexible material and by guide means for guiding strip 20 in its longitudinal direction. Strip 20 extends through fixation element 7, coupling piece 5 and inside housing 1. Strip 20 is bent for this purpose. By displacing strip 20 in its longitudinal direction the part of strip 20 bent by its guide means will be displaced, which requires strip 20 to be flexible.

Figure 4:
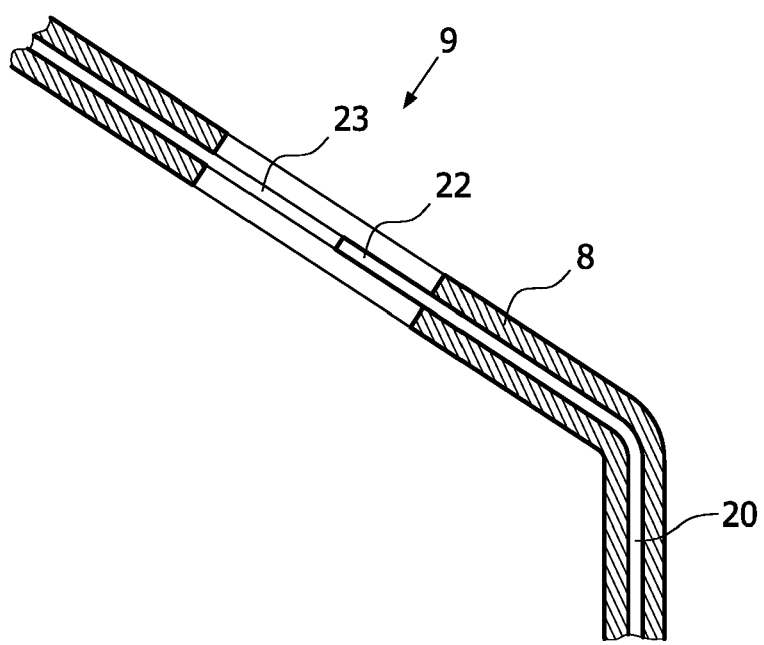
FIG. 4 shows a detail of the view depicted in FIG. 1.

Strip 20 is shown in more detail in FIG. 4, this in the vicinity of opening 9. This drawing shows that a guide groove 23 is arranged in the thickness of the fixation element for the purpose of guiding the strip 20. Because strip 20 extends not only over the length of opening 9, there is recessed in the remaining part of fixation element 8 a channel 24 through which the strip extends. This channel is otherwise not limited to fixation element 8 but also extends through coupling piece 5 and housing 1. It is noted here that channel 24 does not have to be recessed physically into these components; it is also possible for the channel to be formed implicitly by space that is already available because strip 20 extends inside said components 8, 5, 1. In the latter case it is attractive when guide means are present to guide the strip 20, thereby preventing it from being folded, whereby it would no longer be able to fulfil its function.

As shown in FIG. 1, the end of strip 20 remote from tongues 21 is coupled to a sleeve 25 extending around aerosol housing 3 and aerosol container 2. The sleeve 25 functions as a drive member and a guide for strip 20. It will be apparent that other guide members can be arranged instead of sleeve 25. In one embodiment, the sleeve 25 can serve as a connection between an actuating element 26 for operating strip 20 so as to function as a drive member 25 which runs through a channel 29 in the wall of the collective attachment piece element 33 in its function as engaging means. Actuating element 26 is ergonomically positioned upon sleeve 25 being within reach of actuating element 18 without having to readjust a user's grip on the device. The engaging means 20 are displaced relative to fixation means 8 by sliding the actuating element 26 in axial direction of the cylinder, and the parasite can be engaged.

Figure 5:
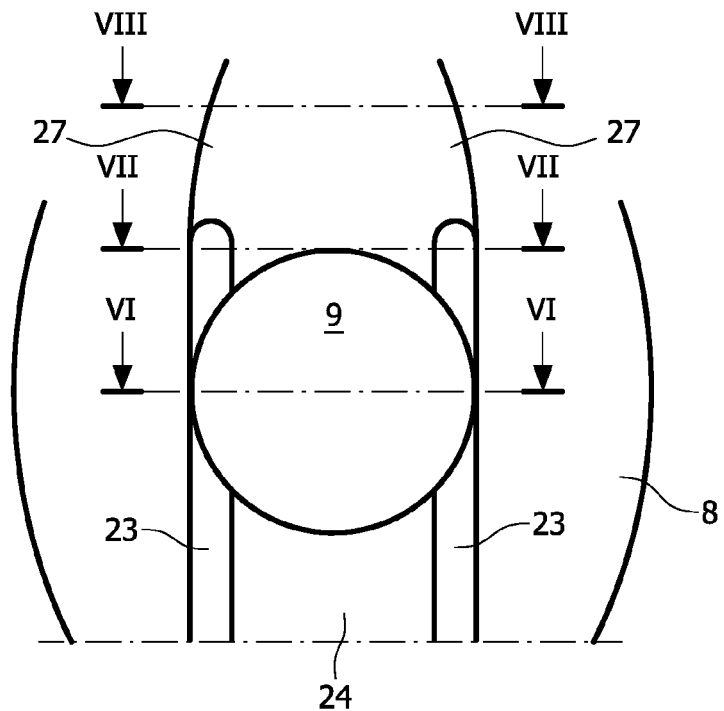
FIG. 5 shows a detail of the view depicted in FIGS. 2 and 3.
Figure 6:
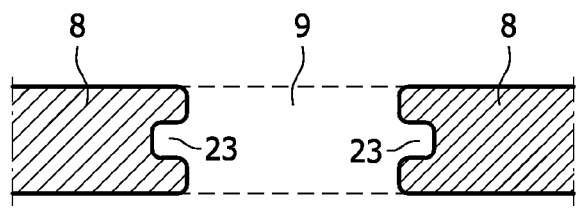
FIG. 6 shows a cross-sectional view along the line VI-VI in FIG. 5.
Figure 7:
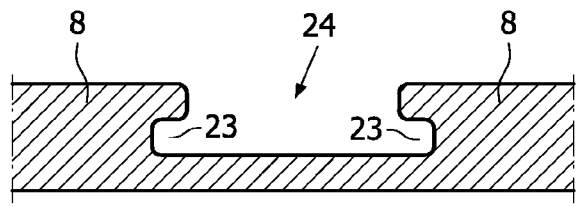
FIG. 7 shows a cross-sectional view along the line VII-VII in FIG. 5.
Figure 8:
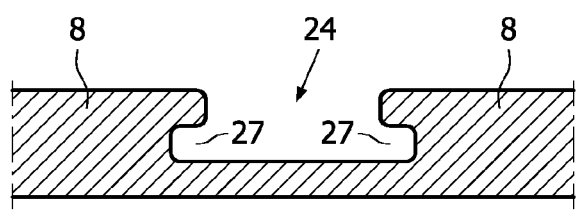
FIG. 8 shows a cross-sectional view along the line VIII-VIII in FIG. 5.
Figure 9:
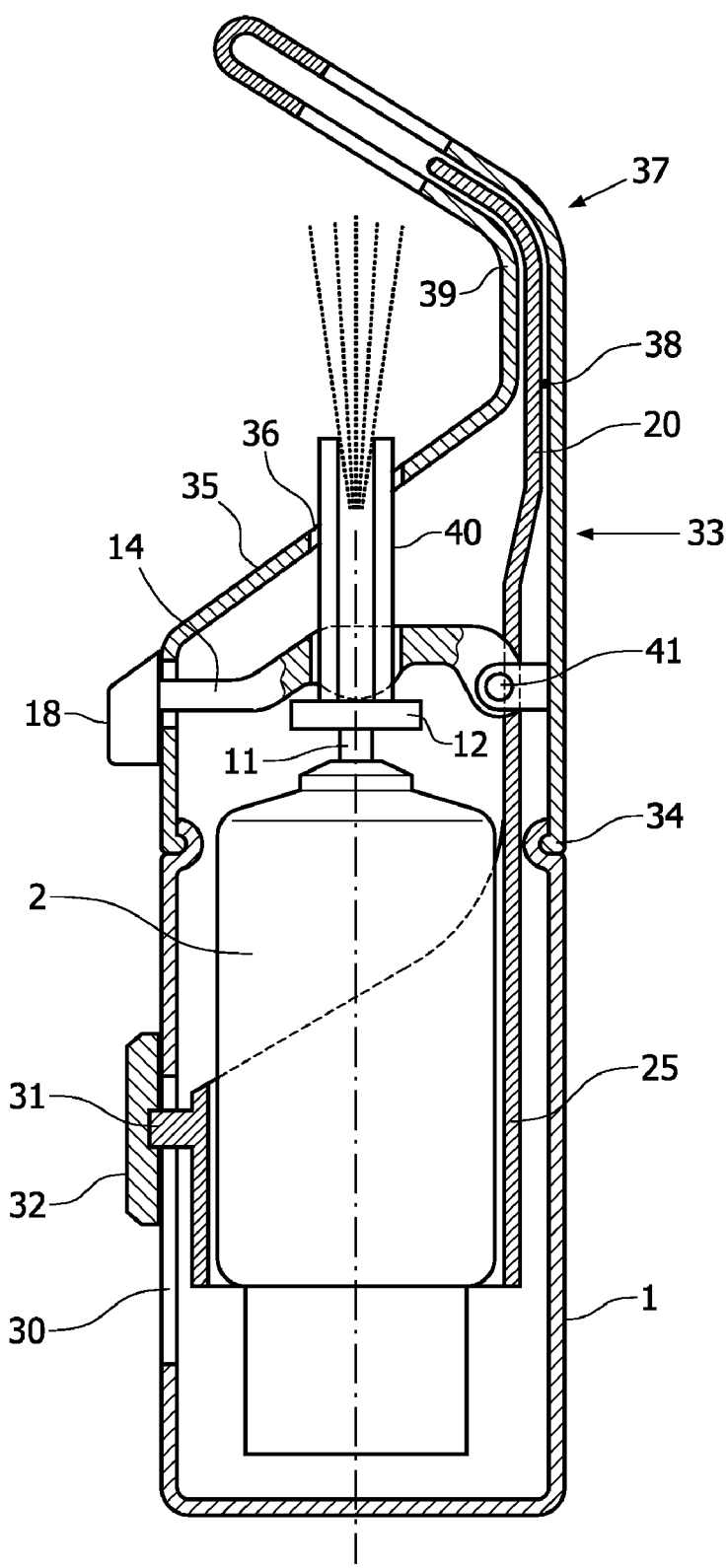
FIG. 9 shows a sectional view corresponding to FIG. 1 of a second embodiment.

The configuration of opening 9 in fixation wall 8 is further shown in FIGS. 5-8. FIG. 5 shows that guide grooves 23 are provided at the end of the opening with converging parts 27 opposite the strip. The tongues 21 of strip 20 are hereby moved toward each other when strip 20 is urged to its extreme position. The notch 22 between tongues 21 is hereby narrowed, whereby the parasite is gripped more firmly.

The operation of the device according to the invention will be elucidated hereinbelow. The fixation wall 8 of the device is placed initially against the skin of the host, this such that the parasite is located in opening 9. The correct placing can herein be monitored through opening 10. The transparent plastic of fixation part 7 moreover makes observation easy.

Once fixation wall 8 lies against the skin of the host, the elongate, substantially cylindrical device extends at an angle between 90° and 30°. This facilitates observation of the parasite. It is pointed out here that the opening is chosen so that most commonly occurring parasites, such as ticks, can be readily placed inside the opening. The maximum size of ticks amounts to about 12 mm. The opening has a diameter of between 10 mm and 15 mm. The size of the opening can otherwise be adapted to the size of the parasite for which the device is suitable.

The valve can then be activated by means of actuating element 18 connected to the valve via the lever. A quantity of aerosol will hereby exit from the valve. The spray head of the valve is placed such that the parasite falls within the aerosol jet. The droplets from the aerosol thus come to lie on the body of the parasite. The liquid of which the aerosol is made up is chosen so that it evaporates as soon as it comes into contact with the body of the parasite. It is not precluded that actuating element 18 must be pressed several times in each case to give a quantity of aerosol to cause cooling of the parasite to a temperature at which it is no longer likely to discharge its digestive organs into its host or at which the parasite no longer disintegrates easily.

When the parasite has reached the desired temperature, it can be removed. To this end the engaging device in the form of the strip is moved toward the parasite using actuating element 26. The strip is moved here such that the parasite is enclosed between tongues 21 of strip 20. This movement is continued until the parasite is touched by the point where the two tongues 21 contact each other. The parasite is then enclosed on three sides by the strip and the tongues. The confinement is even stronger in the preferred embodiment wherein the tongues are pressed toward each other by the converging guides 27.

The whole unit is then moved away from the skin, wherein the parasite is removed from the skin. During the movement away from the skin an edge of the fixation surface can be used as support surface for leverage purposes. It is recommended to move the parasite out of the skin as perpendicularly as possible of the direction of the skin of the host so as to prevent disintegration of the parasite. The tick can subsequently be taken out of the interior and placed in the associated storage space to enable later examination for pathogens. The specific, oblique form of the device is used during the movement away from the skin, as this form can be applied as lever.

It is pointed out here that in the above description reference is made at all times to a combination of an engaging device and administering means for administering an aerosol cooling through evaporation. The invention also relates to a device only suitable for engaging the parasite. The invention also relates to a method performed with this device for engaging the parasite and removal thereof from the skin of its host. The use of this device can optionally be combined with the administering of an aerosol cooling through evaporation.

It is also possible to cover the fixation element when not in use with a separate cover or a separate cap so as to prevent contamination.

FIG. 9 shows a second embodiment, wherein corresponding components are designated with corresponding numerals. Like the first, this embodiment comprises a housing 1 in which an aerosol container 2 is placed. Present between aerosol container 2 and housing 1 is a cylindrical space inside which a sleeve 25 connected to strip 20 is a movable drive member in an axial direction. A slot 30 through which extends a protrusion 31 connected to the sleeve is arranged in housing 1. Attached to protrusion 31 is a slide actuator 32 with which strip 20 is movable via sleeve 25.

So as to provide the user with a better view of the tick, the fixation element and the coupling piece of the previous embodiment are replaced by a collective attachment piece 33 which is connected to housing 1 by means of a snap connection 34 which can optionally be fixed by glue. Attachment piece 33—extending from housing 1—is initially substantially cylindrical. It is then provided with an inclining surface 35 in which is arranged an opening 36 through which extends tube 33.

The inclining surface connects onto a bent tongue-like element 37 which is provided with a channel 38 through which strip 20 extends and in which strip 20 is movable for the purpose of fulfilling the function of engaging the tick, as elucidated with reference to FIG. 1. As a result of this construction the cylindrical part in the vicinity of the fixation means is omitted, thus ensuring a good view of the fixation means and the process taking place there. Side walls limiting the view are no longer present either. The attachment piece takes a double-walled form at the position of tongue-like element 37 in order to enable guiding of strip 20. A certain strength is hereby also obtained. This does however result in problems of production engineering, which are resolved by assembling the coupling piece from two separately formed components which are preferably joined together by glueing.

As in the first embodiment, a lever 14 is arranged for operating the valve 11 which is placed on aerosol container 2 and which is formed in this embodiment by a per se known metering valve. Use is also made here of a collar 12 which is here provided with a tube 33 for guiding the aerosol leaving valve 11. The lever likewise takes a forked form so as to be clear of strip 20 and the tube 20, wherein both ends of the fork are mounted in bearings 38 formed in the attachment piece.

Operations to be carried out with this latter device correspond to the operations to be performed with the first described embodiment.

It will be self-evident that numerous variations can be made to the shown and described device without departing from the invention.

The invention claimed is:

1. A device for removing a parasite from the skin of a human or animal functioning as host, wherein the device comprises:

engaging means for engaging the parasite and removing the parasite from the skin of the host, the engaging means comprising an actuating element which is movable in an axial direction of an aerosol container and can be operated manually, and fixation means for fixing the device on the skin of the host parallel to the skin of the host at least during engaging of the engaging means, wherein the engaging means are adapted to move relative to the fixation means during engaging of the parasite, administering means for the purpose of supplying a cooling medium to at least the parasite, the administering means comprising an aerosol container, received in a housing of the device and an actuating element which can be operated from outside the housing, wherein the actuating element of the administering means can be operated from outside the housing and are connected to a lever connected to the housing for rotation about an axis placed a distance from a valve, and that the actuating element of the engaging means is movable in the axial direction of the aerosol container and can be operated manually wherein the actuating element of the administering means and the actuating element of the engaging means are separately and independently operable to provide greater control over administration of the cooling medium to a parasite and activation of the engaging means, respectively; and further wherein the engaging means comprises a substantially flat structure provided on its edge with a notch; wherein the flat structure is connected for guidable movement to the fixation means by means of a channel in a collective attachment piece element.

2. The device as claimed in claim 1, wherein the device is dimensioned for the purpose of removing a tick (*Ixodidae*).

3. The device as claimed in claim 1, wherein the engaging means are adapted to move substantially parallel to the skin of the host during engaging of the parasite.

4. The device as claimed in claim 1, wherein the notch is provided with two edges converging from the edge of the structure to a point, and that the engaging means are controlled by the actuating element of the engaging means.

5. The device as claimed in claim 4, wherein the edges of the flat structure which are located on the side of the notch are rounded.

6. The device as claimed in claim 4, wherein the fixation means comprise the collective attachment piece element which is provided with an opening and which is adapted to be placed with a substantially flat side against the skin of the host.

7. The device as claimed in claim 6, wherein the flat structure comprises a strip which is manufactured from flexible material and which is connected slidably to a sleeve, wherein the sleeve serves as a drive member that passes through a channel in the collective attachment piece element which is connected slidably to the engaging means.

8. The device as claimed in claim 7, wherein the strip extends outside the collective attachment piece element, and wherein the strip is coupled to the drive member.

9. The device as claimed in claim 1, wherein the administering means are adapted to supply the cooling medium to the parasite in the form of an aerosol jet.

10. The device as claimed in claim 9, wherein the administering means comprises a valve and a spray nozzle, wherein the spray nozzle is placed for directing the aerosol jet, which exits the nozzle when the valve is opened, and passes through an opening in the fixation means.

11. The device as claimed in claim 9, wherein the valve placed on the aerosol container is a metering valve.

12. The device as claimed in claim 10, wherein the aerosol container is substantially cylindrical and that the cylinder axis of the aerosol container extends substantially parallel to the direction of movement of a strip positioned outside the collective attachment piece element.

13. The device as claimed in claim 9, wherein the housing is arranged around the aerosol container, that a drive member is adapted to be guided through a channel on the collective attachment piece, and that the actuating element of the administering means extends through an opening in the aerosol container.

14. The device as claimed in claim 12, wherein the actuating element is substantially cylindrical, that the axis of the cylinder corresponds to the axis of the aerosol container, and that the collective attachment piece element is provided in its outer surface with an opening.

15. The device as claimed in claim 14, wherein the collective attachment piece element is manufactured at least partly from transparent plastic.

16. The device as claimed in claim 1, wherein the device has a substantially cylindrical form, of which the end surface adapted to come into contact with the skin of the host extends at an angle other than 90° from the axis of the cylinder.

17. The device as claimed in claim 1, wherein the device is combined with a storage space for removed parasites.

* * * * *